US00PP36142P2

(12) United States Plant Patent
Dirr et al.

(10) Patent No.: US PP36,142 P2
(45) Date of Patent: Sep. 24, 2024

(54) ***GARDENIA* PLANT NAMED 'ST-15-20'**

(50) Latin Name: *Gardenia jasminoides*
Varietal Denomination: ST-15-20

(71) Applicant: Premier Introductions, Inc., Watkinsville, GA (US)

(72) Inventors: Michael Dirr, Bogart, GA (US); Jeff Beasley, Lavonia, GA (US); Mark Griffin, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/540,154

(22) Filed: Dec. 14, 2023

(51) Int. Cl.
*A01H 6/76* (2018.01)
*A01H 5/00* (2018.01)

(52) U.S. Cl.
USPC ..... Plt./255

(58) Field of Classification Search
USPC ..... Plt./226, 255
See application file for complete search history.

(56) References Cited

U.S. PATENT DOCUMENTS

PP34,958 P2 * 1/2023 Dirr ..... A01H 6/76
Plt./255

* cited by examiner

*Primary Examiner* — Karen M Redden
(74) *Attorney, Agent, or Firm* — Cassandra Bright

(57) ABSTRACT

A new and distinct cultivar of *Gardenia jasminoides* plant named 'ST-15-20', characterized by fragrant, double white flowers, abundant large flowers in spring with reblooming to fall, lustrous, dark green foliage, compact growth habit, cold hardy to USDA Hardiness Zone 7.

3 Drawing Sheets

Genus and species of plant claimed: *Gardenia jasminoides*

Variety denomination: 'ST-15-20'.

BACKGROUND OF THE INVENTION

The present invention relates to a new and distinct cultivar of *Gardenia jasminoides*, a member of the Rubiaceae family, hereinafter referred to by its cultivar name 'ST-15-20'. This cultivar is grown primarily as an ornamental for landscape use and for use as a potted plant.

The new *Gardenia* cultivar originated from an open pollination of *Gardenia jasminoides* 'PIIGA-II', (U.S. Plant Pat. No. 27,258), in Watkinsville, GA, in 2020 and was selected from the progeny by continued evaluation for growth habit, foliage, and floral characteristics.

'ST-15-20' has been asexually reproduced by softwood cuttings in Watkinsville, GA, since 2020, and the characteristics of the cultivar have been stable and reproduced true-to-type in successive vegetative generations.

SUMMARY OF THE INVENTION

'ST-15-20' has not been observed under all possible environmental conditions. The phenotype may vary somewhat with changes in light, temperature, soil, and rainfall without, however, any variance in genotype.

The following traits have been observed and represent the characteristics of the new cultivar. In combination these characteristics distinguish 'ST-15-20' from all other varieties in commerce known to the inventor. 1) Fragrant, large, double white flowers. 2) Abundant flowers in spring with reblooming to fall. 3) Lustrous, dark green foliage. 4) Compact growth habit. 5) Cold hardy to USDA Hardiness Zone 7. There are no other cultivars of *Gardenia* with this combination of characteristics known to the inventors.

PARENTAL COMPARISON

'ST-15-20' is distinguished from its female parent, *Gardenia jasminoides* 'PIIGA-II' (U.S. Plant Pat. No. 27,258), by its size. 'ST-15-20' is more compact with shorter internode length, smaller lustrous dark green foliage, and a smaller overall plant than 'PIIGA-II'.

COMMERCIAL COMPARISONS

'ST-15-20' can be distinguished from 'ST-07-20' (U.S. Plant Pat. No. 34,958) by its habit. 'ST-15-20' has a compact growth habit, whereas 'ST-07-20' has a columnar growth habit.

'ST-15-20' can be compared to 'Chuck Hayes' (US Plant Pat. No. 8,755). 'ST-15-20' is more compact with shorter internodes than 'Chuck Hayes'. 'ST-15-20' is a more prolific rebloomer than 'Chuck Hayes'. 'ST-15-20' is more cold hardy than 'Chuck Hayes'.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new Gardenia. Plants depicted are approximately 2 years old.

DETAILED DESCRIPTION

Figure 1:
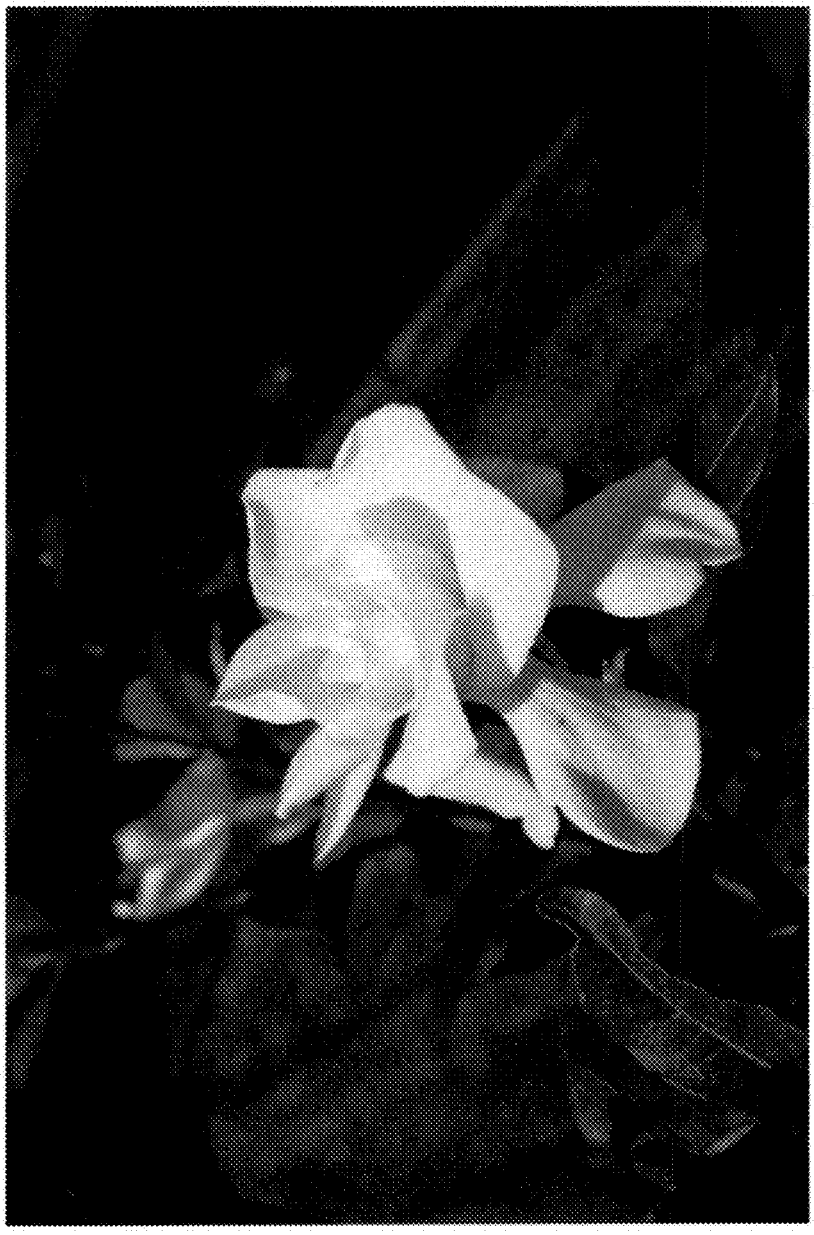
FIG. 1 shows an up-close view of the flower of 'ST-15-20'.
Figure 2:
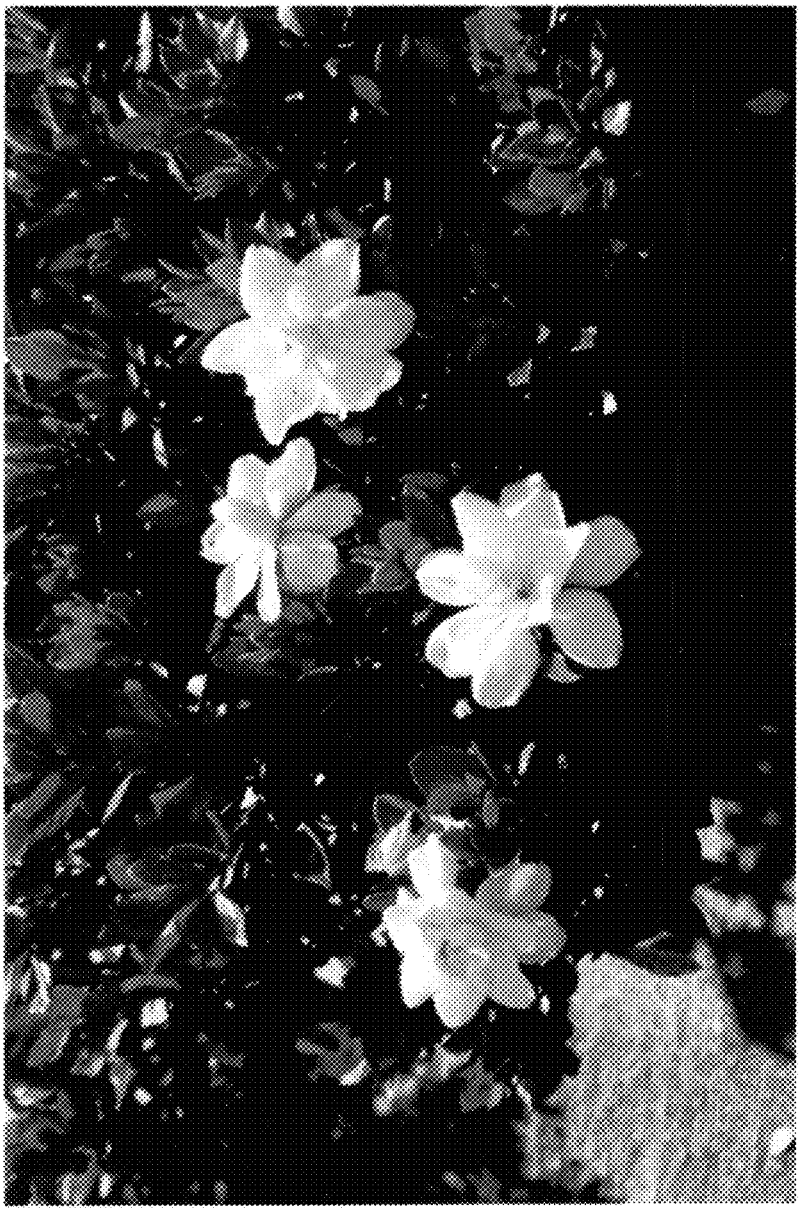
FIG. 2 shows several flowers on a plant of "ST-15-20'.
Figure 3:
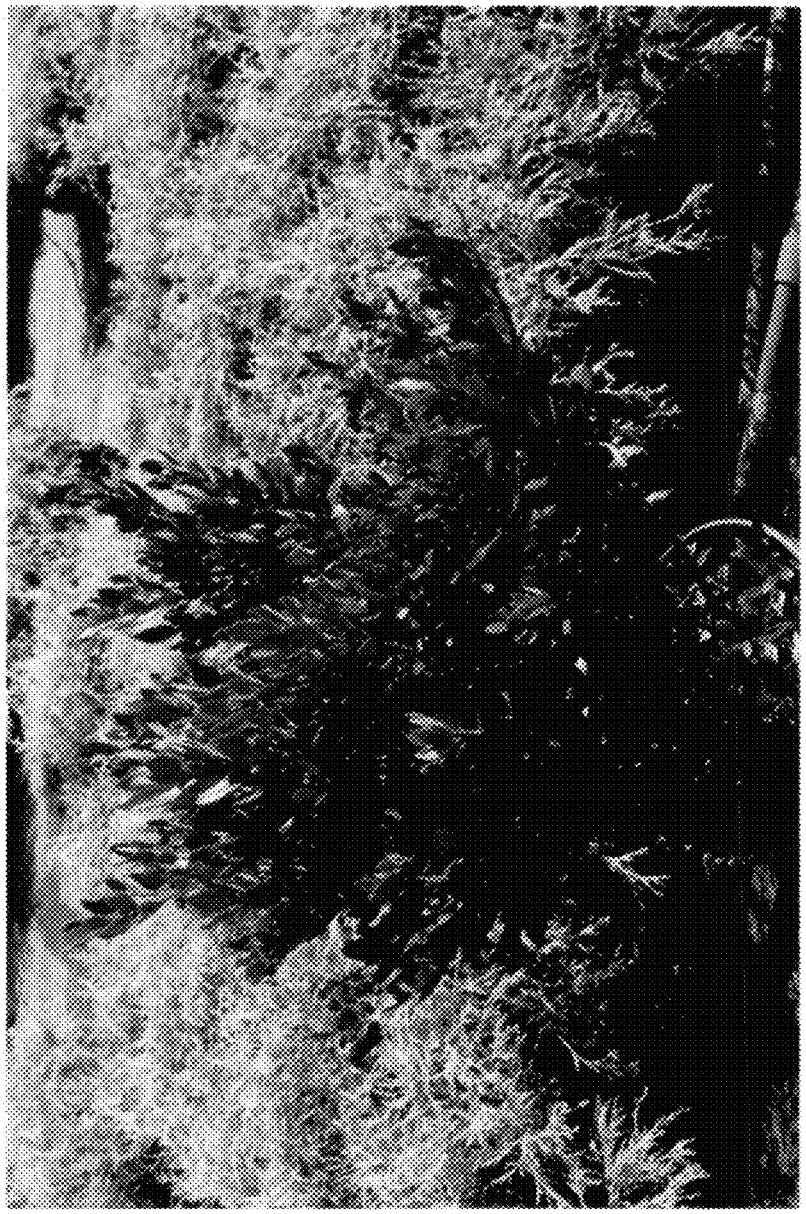
FIG. 3 shows the habit of 'ST-15-20'.

In the following description, color references are made to The Royal Horticultural Society Colour Chart, 2015 Edition, except where general terms of ordinary dictionary significance are used. Plants used for the description were approximately 3 years old and were grown in 11.36 L containers in full sun under outdoor conditions in Watkinsville, GA.

Botanical classification: *Gardenia jasminoides* 'ST-15-20'. Parentage: Female, or seed, parent: *Gardenia jasminoides* 'PIIGA-II' (U.S. Plant Pat. No. 27,258). Male or pollen, parent: unknown (open-pollinated), Propagation: terminal cuttings. Time to initiate roots, summer: about 21 days at 32° C. Time to produce a rooted young plant, summer about 4 months at 32° C.

Plant description: The claimed variety is a freely branching, compact, broadleaf evergreen shrub.

*Propagation*.—stem cuttings. Time to initiate roots in summer: about 21 days.

*Root description*.—numerous, fibrous, and well-branched. Color: 155A.

*Plant size*.—about 44 cm high from the soil level to the top of the foliage and about 58 cm wide after about 2 years. First year stems having a diameter of about 2.5 mm. Length: about 12.5 cm. Shape: terete. Pubescence: finely hairy.

*First year stem color* (*young*).—143B. Color (woody): N200B.

*Stem strength*.—flexible when young, more easily broken once mature.

*Internode length*.—1 to 1.5 cm. Second year and older stems have a diameter of about 5 mm or more. Length: about 37 cm. Internode length: 4 cm. Strength: Stems easily broken once they are mature. Shape: terete. Pubescence: none, lose all pubescence by $2^{nd}$ year.

*Second year and older stem color*.—N200B.

*Bark*.—some stringy exfoliation beginning on second year stems.

*Trunk diameter*.—about 1.7 cm at the soil line. Color: N200B.

Vegetative bud description:

*Vegetative buds*.—Arrangement: opposite. Shape: conical, single-scaled. Size: about 2 mm in length, about 1 mm in width; Color: 143A.

Foliage description:

*Arrangement*.—opposite some whorled, especially at the terminal end of the shoot. Length: about 5 cm. Width: about 2 cm.

*Shape*.—lanceolate. Apex: acuminate. Base: cuneate. Margin: entire.

*Texture* (*upper and lower surfaces*).—glabrous, lustrous.

*Venation*.—pinnate. Venation color upper: 144C. Venation color lower: 144D.

*Color of emerging foliage*.—N144C on the upper surface, and 144B on the lower surface.

*Color of mature foliage*.—147A on the upper surface, and 146D on the lower surface.

*Petiole length*.—about 2 mm. Petiole diameter: about 2 mm. Petiole texture: glabrous. Petiole color (upper and lower surfaces): 144B.

Flower description:

*Flower type and habit*.—flowers are borne singly at the terminals and in the axils where two stems divide. Individual flowers are showy for about 2 days and remain on the plant for about 1 to 2 weeks after they have senesced. Bloom period: spring to frost. Flowers are produced abundantly from May to June, and then sporadically through November in Watkinsville, GA. Fragrance: Exceedingly sweet fragrance.

*Flower diameter*.—about 7 cm. Height or depth: about 4 cm.

*Flower bud diameter*.—about 1.5 cm. Flower bud length: about 3 cm. Flower bud shape: oblong. Flower bud color: 144A.

*Calyx*.—about 2.5 cm in length, about 1.5 cm in width, and 144A in color.

*Sepals*.—Arrangement/quantity: star-shaped calyx with five sepals fused at the base. Length: about 2.5 cm. Width: about 4 mm. Shape: lanceolate. Apex: acute. Margin: entire. Texture on upper and lower surface: smooth, glabrous. Color on upper and lower surface: 144A.

*Peduncles*.—Length: about 1 cm. Diameter: about 4 mm. Angle: upright. Strength: strong. Texture: Smooth, glabrous. Color: 144A.

*Pedicels*.—about 2 cm in length, 6 mm in diameter, glabrous, and 144A in color.

Petals:

*Quantity*.—6 to 8 true petals and 10 to 12 petaloids per flower.

*True petal length*.—about 3.5 cm. Width: about 2 cm. Shape: obovate, Apex: rounded. Base: Attenuate. Margins: entire, undulating and overlapping in arrangement to form a whorl. Texture: thick, glabrous on upper and lower surface. Color: at peak bloom the upper and lower surfaces are NN155B aging to 160B before dehiscing.

*Petaloid length*.—ranges from 1.5 to 2.5 cm, becoming smaller toward the top and center of the flower. Width: ranges from 1.1 to 2.1 cm, becoming smaller toward the top and center of the flower. Shape: Texture: thick, glabrous on upper and lower surface. Color: at peak bloom the upper and lower surfaces are NN155B aging to 160B and before dehiscing.

Stamens:

*Quantity*.—4 to 6 per flower, sometimes petaloid or malformed. There is no separate filament structure present, instead the anthers are fused to the base of the petals. Anthers: about 8 mm long and about 2 mm wide. Shape: Lanceolate. Color: N199D. Pollen: either nonexistent or produced in small quantities and color is 9A.

Pistils:

*Quantity/arrangement*.—one per flower, inferior. Pistil length: about 1.5 cm. Pistil diameter: about 5 mm. Stigma shape: obovate, about 5 mm length and about 4 mm in diameter. Stigma color: 6A. Style: color is 155A, about 2.5 cm in length, and about 1.5 mm in width. Ovary: color is 2B, about 5 mm in length, about 4 mm in width, ellipsoidal in shape, and contains some very small (less than 1 mm) ovules.

Fruit: No mature fruit set observed, year to date.

Plant hardiness: USDA Plant Hardiness Zone Map (2012) Zone 7 to 9.

Disease/pest resistance: No specific pest or disease resistance or susceptibility has been observed.

What is claimed is:

1. A new and distinct cultivar of *Gardenia* plant named 'ST-15-20' as herein illustrated and described.

* * * * *